(12) United States Patent
Bydon et al.

(10) Patent No.: US 11,737,793 B2
(45) Date of Patent: Aug. 29, 2023

(54) FACET JOINT REPLACEMENT DEVICES

(71) Applicant: Mayo Foundation for Medical Education and Research, Rochester, MN (US)

(72) Inventors: Mohamad Bydon, Rochester, MN (US); Chunfeng Zhao, Rochester, MN (US); Hugo Giambini, San Antonio, TX (US); Brandon A. McCutcheon, Rochester, MN (US); Panagiotis Kerezoudis, Rochester, MN (US); Timothy L. Rossman, Rochester, MN (US); Allen K. Rech, Oronoco, MN (US); Joel L. Kuhlmann, Rochester, MN (US); Mohammed Ali Alvi, Rochester, MN (US); Daniel J. Mangiameli, Worcester, MA (US); Robert A. Highet, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/757,529

(22) PCT Filed: Oct. 10, 2018

(86) PCT No.: PCT/US2018/056488
§ 371 (c)(1),
(2) Date: Apr. 20, 2020

(87) PCT Pub. No.: WO2019/079581
PCT Pub. Date: Apr. 25, 2019

(65) Prior Publication Data
US 2021/0186574 A1 Jun. 24, 2021

Related U.S. Application Data

(60) Provisional application No. 62/575,196, filed on Oct. 20, 2017.

(51) Int. Cl.
*A61B 17/70* (2006.01)
*A61F 2/44* (2006.01)
(Continued)

(52) U.S. Cl.
CPC ........ *A61B 17/7064* (2013.01); *A61F 2/4405* (2013.01); *A61B 2017/00862* (2013.01); *A61F 2002/3055* (2013.01)

(58) Field of Classification Search
CPC ............ A61B 17/7064; A61B 17/7062; A61B 17/7019; A61B 17/7023; A61B 17/7025; A61F 2/4405; Y10T 403/32557
See application file for complete search history.

(56) References Cited

U.S. PATENT DOCUMENTS

| 5,375,823 A | 12/1994 | Navas |
| 6,241,730 B1 | 6/2001 | Alby |

(Continued)

OTHER PUBLICATIONS

Businesswire.com' [BusinessWire] "Research and Markets: US Spinal Surgery Devices Market: Increasing Procedures to Drive Growth," Dec. 14, 2009, Retrieved Mar. 8, 2018, Retrieved online: URL<https://www.businesswire.com/news/home/20091214005893/en/Research-Markets-Spinal-Surgery-Devices-Market-Increasing>, 5 pages.

(Continued)

*Primary Examiner* — Jan Christopher L Merene
(74) *Attorney, Agent, or Firm* — Fish & Richardson P.C.

(57) ABSTRACT

Devices and systems can be used to treating spinal conditions. For example, this document describes artificial facet joint systems that can be implanted to treat spinal conditions while facilitating normal stability and motions of the spine. Such systems and methods can be used to treat spinal conditions such as, but not limited to, spondylosis, vertebral fractures, and the like.

7 Claims, 6 Drawing Sheets

(51) Int. Cl.
*A61B 17/00* (2006.01)
*A61F 2/30* (2006.01)

(56) References Cited

U.S. PATENT DOCUMENTS

| | | | |
|---|---|---|---|
| 7,744,633 B2 | 6/2010 | BerreVoets et al. | |
| 7,862,586 B2 | 1/2011 | Malek | |
| 7,935,134 B2 | 5/2011 | Reglos et al. | |
| 8,070,783 B2 | 12/2011 | Kwak et al. | |
| 8,202,301 B2 | 6/2012 | Prevost et al. | |
| 8,226,688 B2 | 7/2012 | Alain | |
| 8,287,571 B2 * | 10/2012 | Semler | A61B 17/7031 606/254 |
| 8,353,933 B2 | 1/2013 | Triplett et al. | |
| 8,709,043 B2 | 4/2014 | Kwak et al. | |
| 9,017,385 B1 * | 4/2015 | Law | A61B 17/7041 606/257 |
| 9,072,544 B2 | 7/2015 | Fortin et al. | |
| 2004/0049190 A1 | 3/2004 | Biedermann et al. | |
| 2005/0113922 A1 | 5/2005 | Brazenor | |
| 2005/0124991 A1 | 6/2005 | Jahng | |
| 2005/0165396 A1 * | 7/2005 | Fortin | A61B 17/7025 606/907 |
| 2005/0222569 A1 | 10/2005 | Panjabi | |
| 2006/0036240 A1 * | 2/2006 | Colleran | A61B 17/7062 606/279 |
| 2006/0189984 A1 * | 8/2006 | Fallin | A61B 17/7052 606/250 |
| 2006/0247637 A1 * | 11/2006 | Colleran | A61B 17/7014 606/279 |
| 2006/0265074 A1 * | 11/2006 | Krishna | A61B 17/7064 606/279 |
| 2007/0032123 A1 | 2/2007 | Timm et al. | |
| 2008/0027436 A1 | 1/2008 | Cournoyer et al. | |
| 2008/0033562 A1 | 2/2008 | Krishna et al. | |
| 2008/0195208 A1 * | 8/2008 | Castellvi | A61B 17/7025 623/17.15 |
| 2008/0275507 A1 * | 11/2008 | Triplett | A61B 17/707 606/278 |
| 2009/0030465 A1 * | 1/2009 | Altarac | A61B 17/7023 606/264 |
| 2009/0048631 A1 | 2/2009 | Bhatnagar et al. | |
| 2009/0099608 A1 | 4/2009 | Szczesny | |
| 2009/0187219 A1 * | 7/2009 | Pachtman | A61B 17/683 606/324 |
| 2010/0069964 A1 * | 3/2010 | Lechmann | A61B 17/7025 606/246 |
| 2010/0211104 A1 | 8/2010 | Moumene et al. | |
| 2011/0238119 A1 | 9/2011 | Moumene et al. | |
| 2011/0282391 A1 | 11/2011 | Dall | |
| 2013/0078027 A1 * | 3/2013 | Hsu | G06F 1/1681 403/113 |
| 2013/0123854 A1 * | 5/2013 | Kondrashov | A61B 17/7038 606/264 |
| 2013/0338713 A1 | 12/2013 | Kawakami et al. | |
| 2016/0278814 A1 | 9/2016 | Seme et al. | |
| 2018/0071106 A1 * | 3/2018 | Bydon | A61B 17/7031 |

OTHER PUBLICATIONS

Criswell, Amy Jo., "Development of a lumbar facet joint replacement," MS (Master of Science) thesis, University of Iowa, 2013, URL<http://ir.uiowa.edu/etd/2466>, 107 pages.

Gomleksiz et al., "A short history of posterior dynamic stabilization," Advances in Orthopedics, 2012, Article ID 629698, 12 pages.

Gornet et al., "Cervical disc arthroplasty with PRESTIGE LP disc versus anterior cervical discectomy and fusion: a prospective, multicenter investigational device exemption study," J. Neurosurg Spine, Nov. 2015, 23(5):558-573.

International Preliminary Report on Patentability in International Application No. PCT/US2018/056488 dated Apr. 21, 2020, 7 pages.

International Search Report & Written Opinion in International Application No. PCT/US2018/056488 dated Jan. 18, 2019, 14 pages.

Lotz et al., "Compression-Induced Degeneration of the Intervertebral Disc: An in Vivo Mouse Model and Finite-Element Study," Spine, Dec. 1998, 23(23):2493-506.

Nayak et al., "Postero-lateral disc prosthesis combined with a unilateral facet replacement device maintains quantity and quality of motion at a single lumbar level," International J Spine Surgery., 2014, 19 pages.

Rajaee et al., "Spinal fusion in the United States," Spine, Jan. 2012, 37(1):67-76.

Rannou et al., "Cyclic tensile stretch modulates proteoglycan production by intervertebral disc annulus fibrosus cells through production of nitrite oxide," Journal of cellular biochemistry, Sep. 2003, 90(1):148-157.

Serhan et al., "Motion-preserving technologies for degenerative lumbar spine: The past, present, and future horizons," SAS J., 5:75-89, 2011.

Yoshihara et al., "National trends in the United States, 2000 to 2009," Spine, Feb. 2015, 15(2):265-271.

YouTube.com' [Online Video]. "Alphatec spine—Isobar dynamicrod," Published on Jul. 16, 2014, [Retrieved Mar. 8, 2018] Retrieved from the Internet: URL: https://www.youtube.com/watch?v=ITLbt8zrLlQ, 2 pages.

* cited by examiner

FACET JOINT REPLACEMENT DEVICES

CROSS-REFERENCE TO RELATED APPLICATIONS

This application is a National Stage application under 35 U.S.C. § 371 of International Application No. PCT/US2018/056488, having an International Filing Date of Oct. 18, 2018, which claims the benefit of U.S. Provisional Application Ser. No. 62/575,196, filed Oct. 20, 2017. The disclosure of the prior applications are considered part of (and are incorporated by reference in) the disclosure of this application.

BACKGROUND

1. Technical Field

This document relates to devices and systems for treating spinal conditions. For example, this document relates to artificial facet joint systems that can be implanted to treat spinal conditions while facilitating substantially normal stability and motions of the spine.

2. Background Information

Low back pain (LBP) and neck pain are among the most common patient complaints in the primary care setting. Globally, LBP has been ranked as the greatest contributor to worldwide disability with an estimated annual direct medical cost over $100 billion. According to most recent studies, the mean annual prevalence of LBP is 9-13%, with a lifetime risk up to 65%. Since the mean life expectancy continues to rise in the US population, the number of people with LBP will increase substantially.

The major cause of LBP and neck pain is spondylosis (i.e., degenerative spinal disease); especially amongst the elderly. Though non-operative management strategies can be efficacious, many patients ultimately require surgical treatment of the affected vertebral level. Traditionally, such operations have involved fusion of the spine, which includes placing screws at the vertebrae and a small rod that connects the screws together.

Apart from spondylosis, another widespread application of spinal fusion is for the treatment of vertebral fractures secondary to osteoporosis. Approximately 8 million women and 2 million men suffer from this condition. Another 34 million have low bone mass and are thus at increased risk for osteoporosis. Moreover, an estimated 700,000 of these patients will experience a vertebral compression fracture that will necessitate spinal fusion in order to preserve spinal stability. Current analyses forecast that osteoporosis will continue to increase in prevalence significantly over the next 20 years.

Spinal fusion is an option for the management of spondylosis or fractures secondary to osteoporosis. Spinal fusion has the benefit of allowing for removal of degenerative tissue while simultaneously preserving spinal stability. However, it comes at the cost of reduced range of motion.

SUMMARY

This document provides devices and systems for treating spinal conditions. For example, this document provides artificial facet joint systems that can be implanted to treat spinal conditions while facilitating normal stability and motions of the spine. The systems and methods provided herein can be used to treat spinal conditions such as, but not limited to, spondylosis, spondylolisthesis, cervical or lumbar stenosis, foraminal stenosis, vertebral fractures, and the like.

In one aspect, this disclosure is directed to a facet joint replacement device. The facet joint replacement device can include a housing defining an opening, an internal space, and a channel, a first rod slidingly engaged with the opening, the first rod including an internal end portion disposed within the internal space and an external end portion disposed outside of the internal space, the first rod also including a projection extending from the internal end portion and disposed within the channel, and a second rod extending from the housing opposite the opening. In some cases, the first rod and the second rod can be compressed toward each other such that a portion of the external end portion of the first rod enters the internal space. In some cases, the first rod and the second rod can be pulled away from each other such that a portion of the internal end portion of the first rod exits the internal space. In some cases, the first rod can be limited in rotation around its longitudinal axis by the projection disposed in the channel. In some cases, the housing can have a non-circular cross-sectional shape. In some cases, the housing can have an ovular cross-sectional shape. In some cases, the housing can be arced along a longitudinal axis. In some cases, the facet joint replacement device can include an elastic element disposed within the internal space. In some cases, the opening can be ovular.

In another aspect, this disclosure is directed to a facet joint replacement device. In some cases, the facet joint replacement device can include a housing defining an opening and an internal space, a first rod slidingly engaged with the opening, the first rod including an internal end portion disposed within the internal space and comprising a head with a head diameter greater than a diameter of other portions of the first rod, the first rod also comprising an external end portion disposed outside of the internal space, and a second rod extending from the housing opposite the opening. In some cases, the first rod and the second rod can be compressed toward each other such that a portion of the external end portion of the first rod enters the internal space. In some cases, the first rod and the second rod can be pulled away from each other such that a portion of the internal end portion of the first rod exits the internal space. In some cases, the housing can have a non-circular cross-sectional shape. In some cases, the housing can have an ovular cross-sectional shape. In some cases, the housing can be arced along a longitudinal axis. In some cases, the facet joint replacement device can include an elastic element disposed within the internal space. In some cases, the elastic element can be disposed between the head and the opening. In some cases, the elastic element can be disposed between the head and a portion of the internal space located near the second rod. In some cases, the elastic element can be coupled to the head. In some cases, an internal diameter of the housing can decrease as the housing extends away from a horizontal axis of the housing. In some cases, the head can be sized such that resistance between the head and the internal diameter of the housing increases as the internal diameter of the housing decreases.

In another aspect, this disclosure is directed to a facet joint replacement device. The facet joint replacement device can include a housing defining a first opening and a first internal space, an insert defining a second opening and a second internal space, wherein the insert is configured to be disposed within the first internal space, a first rod slidingly engaged with the first opening, the first rod including an internal end portion disposed within the second internal space and comprising a head with a head diameter greater than a diameter of other portions of the first rod, the first rod also comprising an external end portion disposed outside of the first internal space, and a second rod extending from the housing opposite the first opening. In some cases, the first rod and the second rod can be compressed toward each other such that a portion of the external end portion of the first rod enters the first internal space or the second internal space. In some cases, the first rod and the second rod can be pulled away from each other such that a portion of the internal end portion of the first rod exits the first internal space or the second internal space. In some cases, the housing can have a non-circular cross-sectional shape. In some cases, the housing can have an ovular cross-sectional shape. In some cases, the housing can be arced along a longitudinal axis. In some cases, the insert can be arced along a longitudinal axis. In some cases, the insert can be an elastic element. In some cases, the elastic element can be an elastomer. In some cases, an internal diameter of the insert can decrease as the insert extends away from a horizontal axis of the insert. In some cases, the head can be sized such that resistance between the head and the internal diameter of the insert increases as the internal diameter of the insert decreases.

In another aspect, this disclosure is directed to a method of treating a spinal condition. The method can include removing facet joint bone matter of adjacent vertebrae, installing two cortical screws or lateral mass screws in each vertebrae of the adjacent vertebrae, and coupling two facet joint replacement devices to the cortical screws or lateral mass screws. In some cases, each facet joint replacement device can include a housing defining an opening and an internal space, a first rod slidingly engaged with the opening, the first rod including an internal end portion disposed within the internal space and an external end portion disposed outside of the internal space, and a second rod extending from the housing opposite the opening.

Particular embodiments of the subject matter described in this document can be implemented to realize one or more of the following advantages. In some embodiments, spinal conditions, such as spondylosis, vertebral fractures, and the like, can be treated using the devices and methods provided herein. The artificial facet joint devices and systems provided herein maintain the natural facet joint center of rotation. Hence, the devices and systems can be implanted to treat spinal conditions while advantageously facilitating normal stability and motions of the spine. The devices provided herein can utilize lateral mass screws (cervical spine) or cortical bone trajectory screws (thoraco-lumbar spine) rather than traditional pedicle screws. The use of such cortical screws is advantageous because they can be anchored to solid bone and preserve motion in the center of the vertebral body. Further, the use of cortical screws with the devices provided herein enables the artificial facet joints to be located near to where the natural facet joint was previously anatomically located (prior to its removal for installation of the artificial facet joint). Hence, a substantially naturally-behaving (from a biomechanical standpoint) artificial facet joint can be attained using the artificial facet joint systems provided herein. Moreover, in some embodiments, various spinal conditions can be advantageously treated in a minimally invasive fashion using the systems and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers represent corresponding parts throughout.

DETAILED DESCRIPTION

This document provides devices and systems for treating spinal conditions. For example, this document provides artificial facet joint systems that can be implanted to treat spinal conditions while facilitating normal stability and motions of the spine (including limitations to such motions). The systems and methods provided herein can be used to treat spinal conditions such as, but not limited to, spondylosis, spondylolisthesis, spinal stenosis, foraminal stenosis, vertebral fractures, osteoporosis, and the like.

The facet joints play a pivotal role in spinal biomechanics. In the lumbar and cervical spine, the major role of the facet joint is to allow for flexion and extension. To a lesser degree, lateral bending and axial rotation also occur about this joint. In some cases, the facet joint can carry up to 25% of a spinal axial compression load.

In view of the facts above, artificial facet joint devices would preferentially allow for the following motions: flexion, extension, lateral bending, axial compression, axial tension, and axial rotation. Moreover, it is desirable to use a device that can achieve such motions while also maintaining the natural facet joint center of rotation and natural limitations on such motions.

This disclosure describes facet joint replacement (FJR) systems that would allow surgeons to perform an inferior facetectomy (a common procedure in both the cervical and lumbar spine) or similar surgical technique in which the natural facet joints would be removed and effectively replaced with an artificial facet joint. Such artificial FJR systems will preserve to a first order approximation the natural biomechanics of the facet joint.

Figure 1:
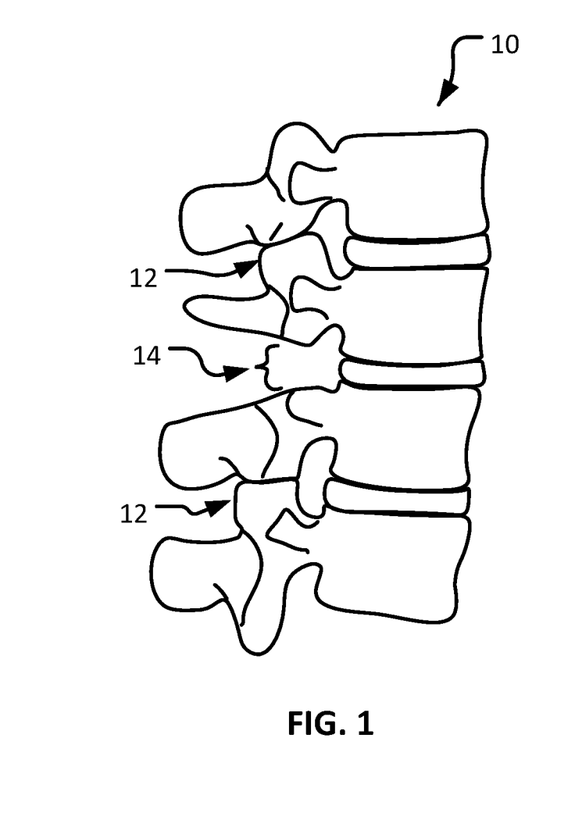
FIG. 1 is a lateral view of a portion of a spine that has had facet joints surgically removed in preparation for the installation of artificial facet joints.

Referring to FIG. 1, a portion of a spine 10 can be prepared to receive an artificial FJR system as provided herein. In this example, the spinal portion 10 has undergone an inferior facetectomy. In some cases, other similar surgical techniques in which the facet joints, or portions thereof, are removed can be performed in preparation to receive an artificial FJR system as provided herein.

Spinal portion 10 includes natural facet joints 12. However, in this example spinal portion 10 has facet joints removed in region 14. The removal of the natural facet joint in region 14 can be performed in preparation for the installation of an artificial FJR system as provided herein. In some cases, the removal of the natural facet joint in region 14 can be performed in a minimally-invasive manner.

Figure 2:
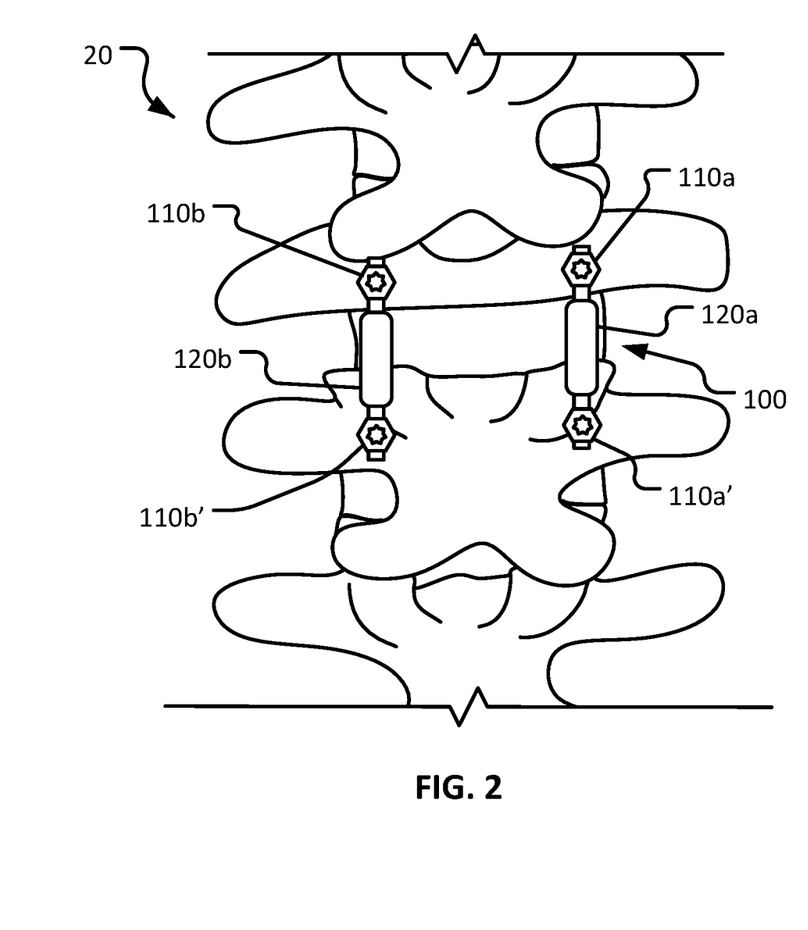
FIG. 2 is a posterior view of a portion of a spine in which an example artificial facet joint system has been installed in accordance with some embodiments provided herein.

Referring to FIG. 2, an example artificial FJR system 100 can be installed in a spinal portion 20 to substitute for the function of a removed natural facet joint. Artificial FJR system 100 can be implanted to treat spinal conditions while facilitating substantially normal stability and motions of the spine 20. In some cases, in addition to installing artificial FJR system 100, one or more prosthetic elements that simulate intervertebral discs can be installed between adjacent vertebrae.

In some cases, artificial FJR system 100 can allow for the following motions: flexion, extension, lateral bending, axial compression, axial tension, and rotation. In addition, artificial FJR system 100 can facilitate such motions while also substantially maintaining the natural facet joint center of rotation.

In some embodiments, artificial FJR system 100 is structurally designed to allow limited amounts of displacement related to the aforementioned motions. Moreover, in some embodiments the resistance provided by artificial FJR system 100 to displacements from such motions can be linear, or non-linear. For example, in some embodiments non-linear resistance to displacements can be provided by artificial FJR system 100 such that the resistance substantially increases as the structural limitations on the displacements are neared.

In the depicted embodiment, artificial FJR system 100 includes a first pair of cortical trajectory screws (cortical screws) 110a and 110a', a first facet joint replacement device 120a, a second pair of cortical screws 110b and 110b', and a second facet joint replacement device 120b. First facet joint replacement device 120a is fixedly joined to, and extending between, cortical screw 110a and cortical screw 110a'. Second facet joint replacement device 120b is fixedly joined to, and extending between, cortical screw 110b and cortical screw 110b'.

In some cases, cortical screws 110a, 110a', 110b, and 110b' can be the same as, or similar to, the types of cortical screws that are installed along with rods as part of a spinal fusion system. The cortical screws 110a, 110a', 110b, and 110b' may also be referred to as cortical bone trajectory screws (for thoracolumbar applications) and lateral mass screws (for cervical applications). One example of such cortical screws (for thoracolumbar) is the VIPER® Cortical Fix Screw from DePuy Synthes (a Johnson & Johnson company), which can be used for this application. One example of lateral mass screws (for cervical applications) is the MOUNTAINEER® OCT Spinal System also from DePuy Synthes. Other companies make similar screws. Such cortical screws 110a, 110a', 110b, and 110b' can be installed (i.e., affixed to vertebrae) using a minimally-invasive surgical procedure in some cases. Other types of fixation devices can additionally or alternatively be used.

Facet joint replacement devices 120a and 120b extend between first pair of cortical screws 110a and 110a' and second pair of cortical screws 110b and 110b' respectively. Facet joint replacement devices 120a and 120b thereby replace the function of the natural facet joints that have been removed to make room to install artificial FJR system 100. As described further below, facet joint replacement devices 120a and 120b are designed with multiple degrees of freedom, and with certain physical constraints on those degrees of freedom, so as to mimic the functions and range of motion of natural facet joints.

In some embodiments, one or more laterally-extending stabilizing members (not shown) can be installed between facet joint replacement devices 120a and 120b. The stabilizing members can be completely rigid or can be somewhat flexible. In some embodiments, a single stabilizing member is included that extends between mid-body portions of facet joint replacement devices 120a and 120b. In some embodiments, such stabilizing members are installed in an x-pattern (i.e., a first stabilizing member extends between cortical screws 110a and 110b', and a second stabilizing member extends between 110b and 110a').

Figures 3, 4:
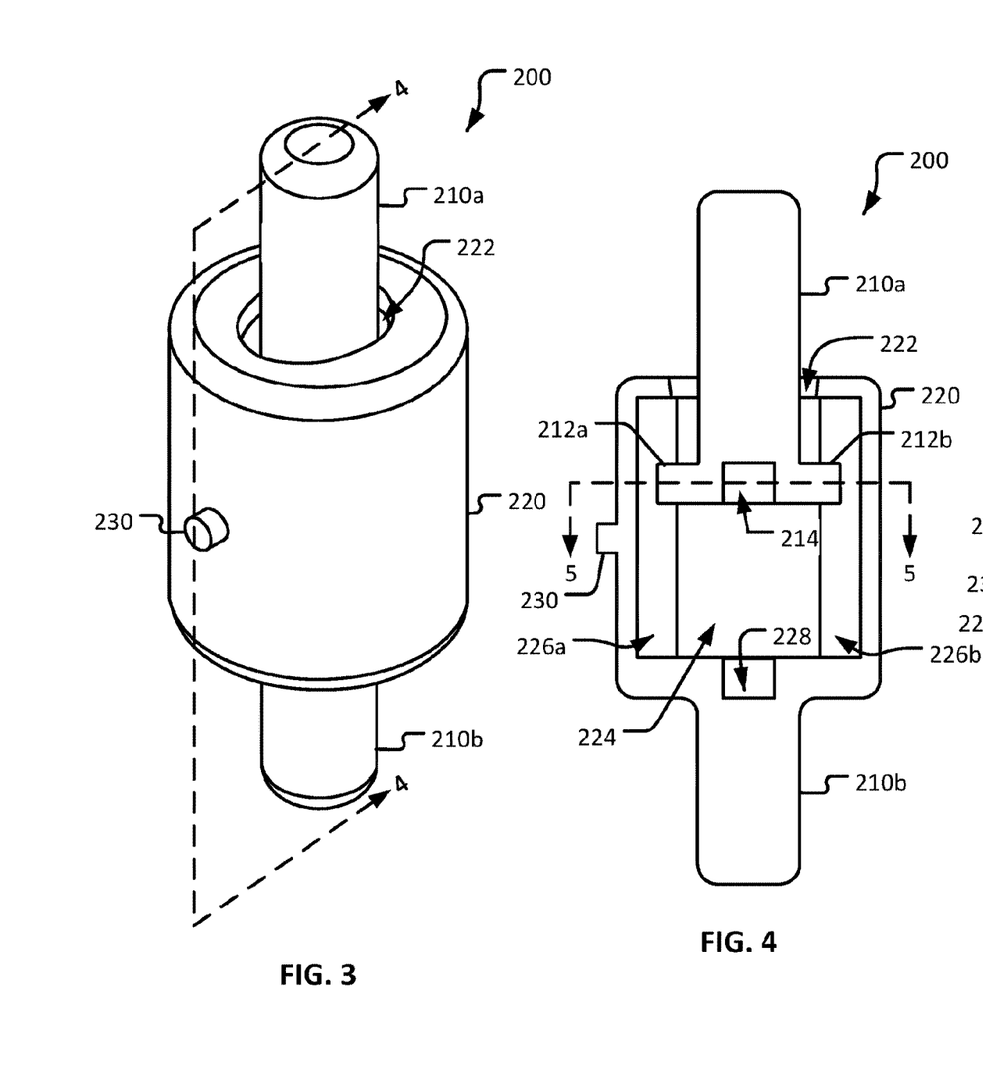
FIG. 3 is an isometric view of an example artificial facet joint device in accordance with some embodiments provided herein.
FIG. 4 is a longitudinal cross-sectional view of the artificial facet joint device of FIG. 3.
Figure 5:
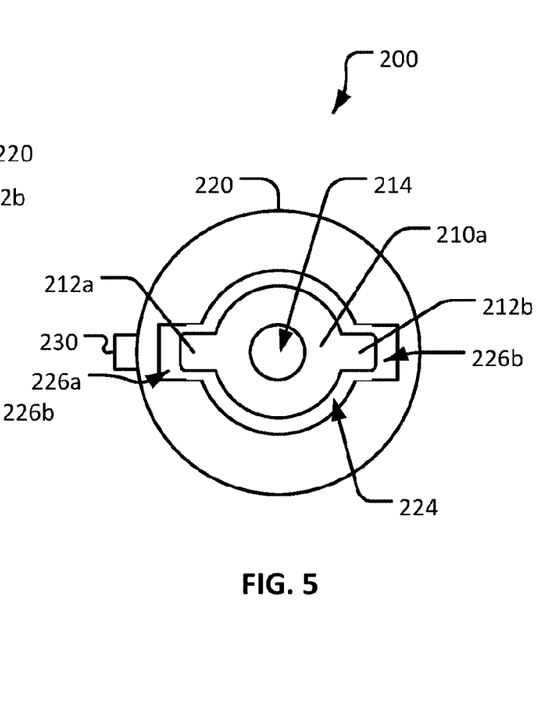
FIG. 5 is a transverse cross-sectional view of the artificial facet joint device of FIG. 4.

Referring to FIGS. 3-5, a facet joint replacement device 200 is an example of the types of facet joint replacement devices that can be used with artificial FJR system 100. Facet joint replacement device 200 can function as a piston/cylinder mechanism. Facet joint replacement device 200 can include a first rod 210a, a second rod 210b, a housing 220, and an opening 222.

First rod 210a and second rod 210b can couple to one of cortical screws 110a, 110a', 110b, or 110b'. First rod 210a can include a first projection 212a and a second projection 212b. First and second projections 212a and 212b can be located opposite one another. In some cases, first and second projections 212a and 212b can be located on a distal portion of first rod 210a. In some cases, first and second projections 212a and 212b can extend perpendicular to first rod 210a. In some cases, first rod 210 can include a cavity 214. In some cases, cavity 214 can receive an elastomeric member. In some cases, the elastomeric member can cushion contact between first rod 210a (e.g., rod projections 212a and 212b) and second rod 210b.

In some cases, first rod 210a and second rod 210b can extend along a single shared axis. In some cases, first rod 210a and second rod 210b extend along different axes. In some cases, second rod 210b can be coupled to, or made unitarily with, housing 220. In some cases, first rod 210a and/or second rod 210b can be linear. In some cases, first rod 210a and/or second rod 210b can be non-linear. In some cases, first rod 210a and/or second rod 210b can be arced to replicate a natural trajectory of a healthy facet joint in extension and flexion. In some cases, the cross-sectional shape of rods 210a and 210b are circular. In some cases, rods 210a and 210b can have other cross-sectional shapes such as, but not limited to, ovular, elliptical, polygonal, and the like.

Housing 220 can be an elongate member that defines an internal space 224. End portion of rod 210a can be movably disposed within the internal space 224 of housing 220. In some cases, facet joint replacement device 200 can be installed such that the rod 210a and internal space 224 are in a neutral position with one another (i.e., no forces acting between the internal space 224 or the rod 210a).

Housing 220, and other portions of facet joint replacement device 200, can be made of various biocompatible metallic or polymeric materials such as, but not limited to, stainless steel, titanium, titanium alloys, cobalt-chrome, nitinol, polyetheretherketone (PEEK), polytetrafluoroethylene (PTFE), perfluoroalkoxy alkanes (PFA), polyvinylidene difluoride (PVDF), and the like, and combinations thereof. In some cases, housing 220 can be made by a molding process. In some cases, housing 220 can be made by a machining process. In some cases, housing 220 and/or one or more other components of facet joint replacement device 200 can be made by a 3D printing method. In some such cases, the design of the component(s) can be customized for a particular patient's spinal anatomy as defined by MR or CT imaging modalities.

In some cases, housing 220 can be cylindrical. In some cases, an exterior diameter of housing 220 can follow an arc that replicates a natural trajectory of a healthy facet joint in extension and flexion. In some cases, an internal diameter of housing 220 can follow an arc that replicates a natural trajectory of a healthy facet joint in extension and flexion. In some cases, housing 220 can have an angled top and/or an angled bottom for the internal space 224 such that when projections 212a and 212b abut the top and/or bottom of the internal space 224, even contact is made between the projections 212a and 212b of first rod 210a and housing 220. In some cases, when projections 212a and 212b come into contact with housing 220 during extension and flexion, projections 212a and 212b can limit range of movement.

Housing 220 can have various cross-sectional shapes. In some cases, the cross-sectional shape of the internal space 224 defined by housing 220 is circular, ovular, elliptical, polygonal, and the like. The cross-sectional shape of the internal space can be selected to allow for a certain amount of free play between rod 210a and an internal wall of housing 220. In some cases, housing 220 can be designed to have some degree of compliance such that housing 220 can bend or flex while in use. In some cases, housing 220 can be designed to be rigid such that housing 220 substantially does not bend or flex while in use.

Housing 220 can include a first channel 226a and second channel 226b. In some cases, first channel 226a and second channel 226b can extend longitudinally along the internal space 224. In some cases, first channel 226a and second channel 226b can align with projections 212a and 212b. In some cases, channels 226a and 226b can be slightly larger than projections 212a and 212b such that channels 226a and 226b can allow a limited amount of side bending and/or axial rotation of the facet joint replacement device 200. In some cases, a size of channels 226a and 226b can determine how much motion is permitted.

In some cases, housing 220 can include a cavity 228 in an internal portion of housing 220. In some cases, cavity 228 can receive an elastomeric member. In some cases, the elastomeric member can cushion contact between first rod 210a (e.g., rod projections 212a and 212b) and a bottom surface of the internal space 224. In some cases, housing 220 can include a projection 230. Projection 230 can provide a visual marker to aid a clinician in placing the facet joint replacement device 200 in the correct orientation.

Housing 220 can define opening 222. Opening 222 can be elliptical such that a greater range of motion is permitted in one direction than a second direction. In some cases, opening 222 can be shaped and sized to allow first rod 210a to follow the arc of housing 220. In some cases, opening 222 can limit motion in lateral bending and/or axial rotation. In some case, opening 222 can be angled to guide the first rod 210a in spine extension and/or flexion. In some cases, the opening 222 can be off-center to allow greater motion in a first direction along a first axis than a second direction along the first axis. In some cases, opening 222 can define an angle. In some cases, the angle can be unique for different locations of the opening 222 such that when movement causes the first rod 210a comes into contact with a wall of the opening 222, an even contact surface is encountered.

In some cases, housing 220 can include one or more inserts. In some cases, an insert can be located at a top portion of the internal space 224 of housing 220. In some cases, an insert can be located at a bottom portion of the internal space 224 of housing 220. In some cases, the insert can be a spring. In some cases, the insert can be an elastic element. In some cases, the elastic element can be made of various materials and can be constructed in various manners. In some cases, the elastic element can be made of a mesh composite. In some embodiments, the elastic element can be an elastic polymeric element. In some cases, the elastic element can be made of a variety of different types of materials and combinations of materials. For example, elastic element can be made of polymeric materials such as, but not limited to, polyurethane, polyethylene, silicone, and other biocompatible elastomers. In some cases, the elastic element can be made of metallic materials such as, but not limited to, nitinol, stainless steel, titanium, titanium alloys, cobalt-chrome, and the like. In some cases, elastic element is solid, but in other cases, elastic element can be constructed for enhanced compliance and/or elasticity. For example, in some embodiments elastic elements, or portions thereof, can be molded, laser-cut, machined, braided, woven, etc. so that the compliance and/or elasticity of elastic element can be enhanced. In some cases, the insert can provide a soft stop at a maximum range of motion in extension and/or flexion.

Figure 6:
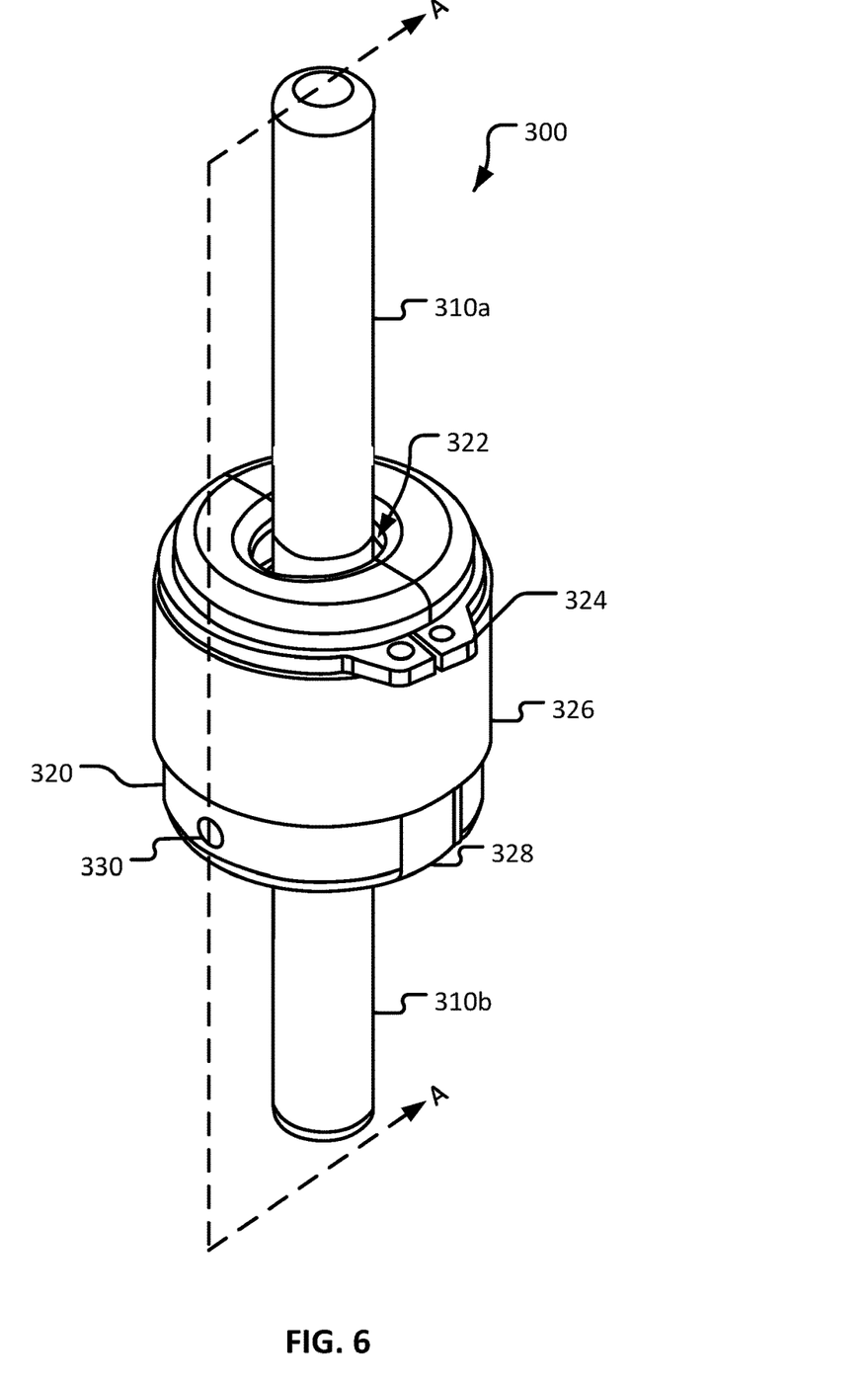
FIG. 6 is an isometric view of an example artificial facet joint device, in accordance with some embodiments provided herein.

Referring to FIG. 6, a facet joint replacement device 300 is another example of the types of facet joint replacement devices that can be used with artificial FJR system 100. Facet joint replacement device 300 can function as a piston/cylinder mechanism. Facet joint replacement device 300 can include a first rod 310a, a second rod 310b, a housing 320, and an opening 322.

First rod 310a and second rod 310b can couple to one of cortical screws 110a, 110a', 110b, or 110b'. In some cases, first rod 310a and second rod 310b can extend along a single axis. In some cases, first rod 310a and second rod 310b extend along different axes. In some cases, second rod 310b can be coupled to housing 320. In some cases, first rod 310a and/or second rod 310b can be linear. In some cases, first rod 310a and/or second rod 310b can be non-linear. In some cases, first rod 310a and/or second rod 310b can be arced to replicate a natural trajectory of a healthy facet joint in extension and flexion. In some cases, the cross-sectional shape of rods 310a and 310b are circular. In some cases, rods 310a and 310b can have other cross-sectional shapes such as, but not limited to, ovular, elliptical, polygonal, and the like.

Housing 320, and the other portions of facet joint replacement device 300, can be made of various biocompatible metallic or polymeric materials such as, but not limited to, stainless steel, titanium, titanium alloys, cobalt-chrome, nitinol, polyetheretherketone (PEEK), polytetrafluoroethylene (PTFE), perfluoroalkoxy alkanes (PFA), polyvinylidene difluoride (PVDF), and the like, and combinations thereof. In some cases, housing 320 can be made by a molding process. In some cases, housing 320 can be made by a machining process. In some cases, housing 320 and/or one or more other components of facet joint replacement device 300 can be made by a 3D printing method. In some such cases, the design of the component(s) can be customized for a particular patient's spinal anatomy as defined by MR or CT imaging modalities. In some cases, housing 320 can be cylindrical. In some cases, an exterior diameter of housing 320 can follow an arc that replicates a natural trajectory of a healthy facet joint in extension and flexion. In some cases, an internal diameter of housing 320 can follow an arc that replicates a natural trajectory of a healthy facet joint in extension and flexion.

Housing 320 can define opening 322. Opening 322 can be elliptical such that a greater range of motion is permitted in one direction than a second direction. In some cases, opening 322 can be shaped and sized to allow first rod 310a to follow an arced path defined by housing 320. In some cases, opening 322 can limit motion in lateral bending and/or axial rotation. In some case, opening 322 can be angled to guide the first rod 310a in spine extension and/or flexion. In some cases, the opening 322 can be off-center to allow greater motion in a first direction along a first axis than a second direction along the first axis. In some cases, opening 322 can define an angle. In some cases, the angle can be unique for different locations of the opening 322 such that when movement causes the first rod 310a comes into contact with a wall of the opening 322, an even contact surface is encountered.

Housing 320 can include a sleeve 326. Sleeve 326 can be shaped to surround the housing 320. In some cases, sleeve 326 can be arced to follow the curvature of housing 320. In some cases, an outer diameter of sleeve 326 can be substantially similar to an outer diameter of housing 320. In some cases, the outer diameter of the sleeve 326 and the outer diameter of the housing 320 being similar can reduce sharp or uneven edges between sleeve 326 and housing 320. In some cases, sleeve 326 can extend along a portion of housing 320. In some cases, sleeve 326 can secure multiple pieces of housing 320 together, such as a top piece and a bottom piece of housing 320. In some cases, housing 320 can be configured as a single unit. In some cases, sleeve 326 can be secured in place via a ring 324.

In some cases, housing 320 can include a recess 328. In some cases, housing 320 can include multiple recesses 328. In some cases, recess 328 can guide a sleeve removal tool 400, shown in FIGS. 13 and 14, along housing 320. In some cases, sleeve 326 can be snuggly fit on housing 320 such that a sleeve removal tool is needed to remove sleeve 326.

In some cases, housing 320 can include a divot 330. In some cases, divot 330 can be used to identify a posterior side of facet joint replacement device 300. In some cases, such as when housing 320 is cylindrical, divot 330 can be used to as an indication of the interior curvature of facet joint replacement device 300. In some cases, facet joint replacement device 330 must be mounted on cortical screws in a specific orientation so that the rotation of first rod 310a takes place in the sagittal plane and the flexion and extension angles are in the correct directions. In some cases, divot 330 can be a physical divot or another type of marker. In some cases, the other type of marker can be a laser printed marker, a printed marker, or other marking on the surface of housing 320.

Figure 7:
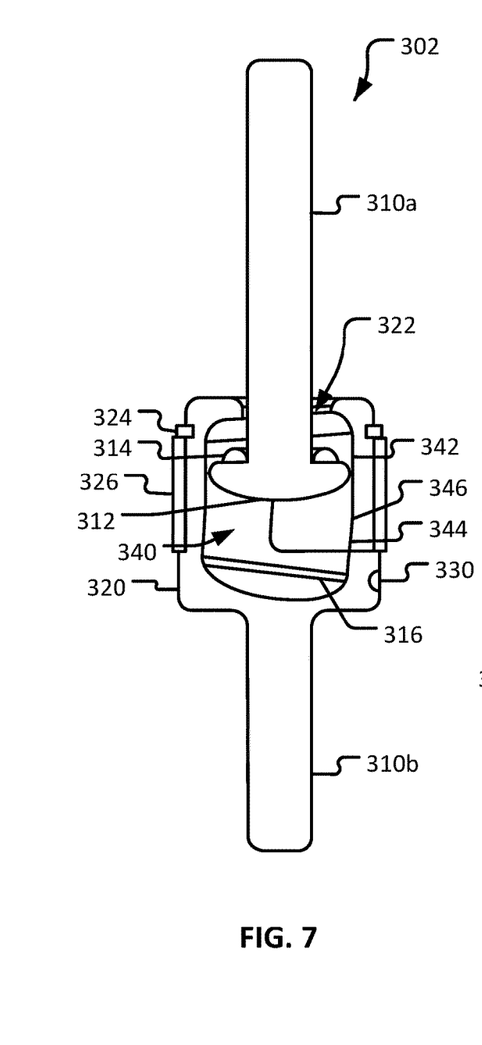
FIG. 7 is a longitudinal cross-sectional view of the artificial facet joint device of FIG. 6.
Figure 8:
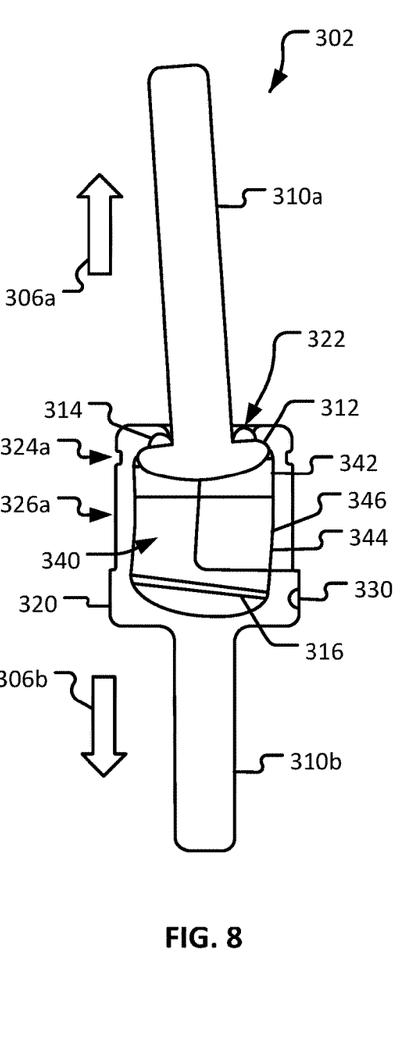
FIG. 8 is a longitudinal cross-sectional view of the artificial facet joint device of FIG. 7, in flexion.
Figure 9:
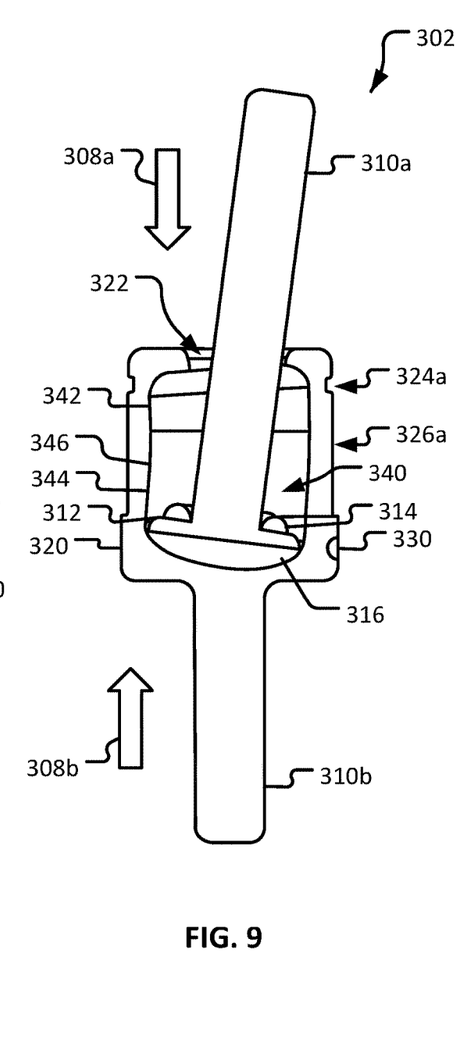
FIG. 9 is a longitudinal cross-sectional view of the artificial facet joint device of FIG. 7, in extension.

Referring to FIGS. 7-9, a facet joint replacement device 302 is an example of the types of facet joint replacement devices that can be used with artificial FJR system 100. Facet joint replacement device 302 can function as a piston/cylinder mechanism and can be substantially similar to facet joint replacement device 300. FIGS. 7-9 show cross section A-A of FIG. 6.

First rod 310a can include a head 312. In some cases, head 312 can be located on a distal portion of first rod 310a. In some cases, head 312 can be rounded. In some cases, head 312 can be mushroom shaped. In some cases, head 312 can be rounded on a distal portion and flat on a proximal portion. In some cases, head 312 can extend perpendicular to the first rod 310a.

In some cases, head 312 can include an insert 314. In some cases, the insert 314 can be a spring. In some cases, insert 314 can be an elastic element. In some cases, the elastic element can be made of various materials and can be constructed in various manners. In some cases, the elastic element can be made of a mesh composite. In some embodiments, the elastic element can be an elastic polymeric element. In some cases, the elastic element can be made of a variety of different types of materials and combinations of materials. For example, elastic element can be made of polymeric materials such as, but not limited to, polyurethane, polyethylene, silicone, and other biocompatible elastomers. In some cases, the elastic element can be made of metallic materials such as, but not limited to, nitinol, stainless steel, titanium, titanium alloys, cobalt-chrome, and the like. In some cases, elastic element is solid, but in other cases, elastic element can be constructed for enhanced compliance and/or elasticity. For example, in some embodiments elastic elements, or portions thereof, can be molded, laser-cut, machined, braided, woven, etc. so that the compliance and/or elasticity of elastic element can be enhanced. In some cases, the insert 314 can provide a soft stop at a maximum range of motion in extension and/or flexion. In some cases, the insert 314 can be coupled to head 312, such that insert 314 and head 312 move in unison. In some cases, insert 314 can be donut shaped to surround rod 310a above head 312.

Housing 320 can be an elongate member that defines an internal space 340. End portion of rod 310a can be movably disposed within the internal space 340 of housing 320. In some cases, facet joint replacement device 302 can be installed such that the rod 310a and internal space 340 are in a neutral position with one another (i.e., no forces acting between the internal space 340 or the rod 310a). In some cases, head 312 can be movably disposed within the internal space 340 of housing 320. In some cases, insert 314 can be coupled to housing 320 in an upper portion of the internal space 340 and can abut head 312 during motion. In some cases, housing 320 can have an angled top and/or an angled bottom for the internal space 340 such that when head 312 and/or insert 314 abut the top and/or bottom of the internal space 340, even contact is made between the head 312 and/or insert 314 of first rod 310a and housing 320. In some cases, when head 312 and/or insert 314 come into contact with housing 320 during extension and flexion, head 312 and/or insert 314 can limit range of movement. In some cases, an internal diameter of housing 320 defining internal space 340 can follow an arc that replicates a natural trajectory of a healthy facet joint in extension and flexion.

Housing 320 can have various cross-sectional shapes. In some cases, the cross-sectional shape of the internal space 340 defined by housing 320 is circular, ovular, elliptical, polygonal, and the like. The cross-sectional shape of the internal space 340 can be selected to allow for a certain amount of free play between rod 310a and an internal wall of housing 320. In some cases, housing 320 can be designed to have some degree of compliance such that housing 320 can bend or flex while in use. In some cases, housing 320 can be designed to be rigid such that housing 320 substantially does not bend or flex while in use.

In some cases, housing 320 can include one or more inserts. In some cases, an insert can be located at a top portion of the internal space 340 of housing 320, as discussed above. In some cases, an insert 316 can be located at a bottom portion of the internal space 340 of housing 320. In some cases, the insert 316 can be a spring. In some cases, the insert 316 can be an elastic element. In some cases, the elastic element can be made of various materials and can be constructed in various manners. In some cases, the elastic element can be made of a mesh composite. In some embodiments, the elastic element can be an elastic polymeric element. In some cases, the elastic element can be made of a variety of different types of materials and combinations of materials. For example, elastic element can be made of polymeric materials such as, but not limited to, polyurethane, polyethylene, silicone, and other biocompatible elastomers. In some cases, the elastic element can be made of metallic materials such as, but not limited to, nitinol, stainless steel, titanium, titanium alloys, cobalt-chrome, and the like. In some cases, elastic element is solid, but in other cases, elastic element can be constructed for enhanced compliance and/or elasticity. For example, in some embodiments elastic elements, or portions thereof, can be molded, laser-cut, machined, braided, woven, etc. so that the compliance and/or elasticity of elastic element can be enhanced. In some cases, the insert can provide a soft stop at a maximum range of motion in extension caused by forces 308a and/or 308b (as shown in FIG. 9) and/or flexion caused by forces 306a and/or 306b (as shown in FIG. 8). In some cases, insert 316 can include channels cut-out of the insert 316 to allow deformation and/or specific a specific amount of resistance. In some cases, insert 316 can extend across internal space 340, leaving a gap between insert 316 and a bottom of the internal space 340. In some cases, insert 316 can rest on a bottom of the internal space 340 and insert 316 can be configured to follow the shape and/or dimensions of the bottom of the internal space 340.

In some cases, internal space 340 can be defined by two or more distinct portions. In some cases, the interior of housing 320 can have an upper portion 342 and a lower portion 344 that conjoin at an inflection region or bend 346 such that internal space establishes a natural trajectory of healthy facet movement. In some cases, upper portion 342 and lower portion 344 can have a diameter that decreases as portions 342 and 344 extend away from bend 346. In some cases, the diameters of upper portion 342 and lower portion 344 can change uniformly. In some cases, the diameters of upper portion 342 and lower portion 344 can change uniquely for each of the upper portion 342 and lower portion 344. In some cases, bend 346 can be a single area where upper portion 342 and lower portion 344 meet. In some cases, bend 346 can be a separate portion with a uniform diameter along bend 346. In some cases, sections of upper portion 342 and/or lower portion 344 can have a consistent diameter before the diameter decreases. In some cases, bend 346 can be oriented in such a way that the movement of first rod 310a follows a natural trajectory of healthy facet movement, which is opposite in direction to the curvature of the lumbar spine vertebrae structure (FIG. 1) in some embodiments. In some cases, bend 346 can have a diameter to allow for a certain amount of free play between rod 310a and an internal wall of housing 320. In some cases, the decrease in diameter of upper portion 342 and/or lower portion 344 can cause an increase of resistance as head 312 and/or first rod 310a moves further along upper portion 342 and/or lower portion 344.

Housing 320 can include a first portion 324a and second portion 326a. In some cases, first portion 324a and second portion 326a can be indents on an exterior of housing 320. In some cases, first portion 324a can aid in securing ring 324. In some cases, second portion 326a can aid in securing sleeve 326. In some cases, first portion 324a can have a depth greater than second portion 326a. In some cases, an exterior diameter of housing 320 can follow an arc that replicates a natural trajectory of a healthy facet joint in extension and flexion. In some cases, housing 320 can have a uniform exterior, such that portions 324a and 326a are not included (e.g., when housing 320 does not include ring 324 and/or sleeve 326). In some cases, portions 324a and 326a can be two separate pieces of housing 320. In some cases, sleeve 326 and ring 324 can hold portions 324a and 326a of housing 320 together. In some cases, portions 324a and 326a can be used to allow housing 320 to receive head 312.

Figure 10:
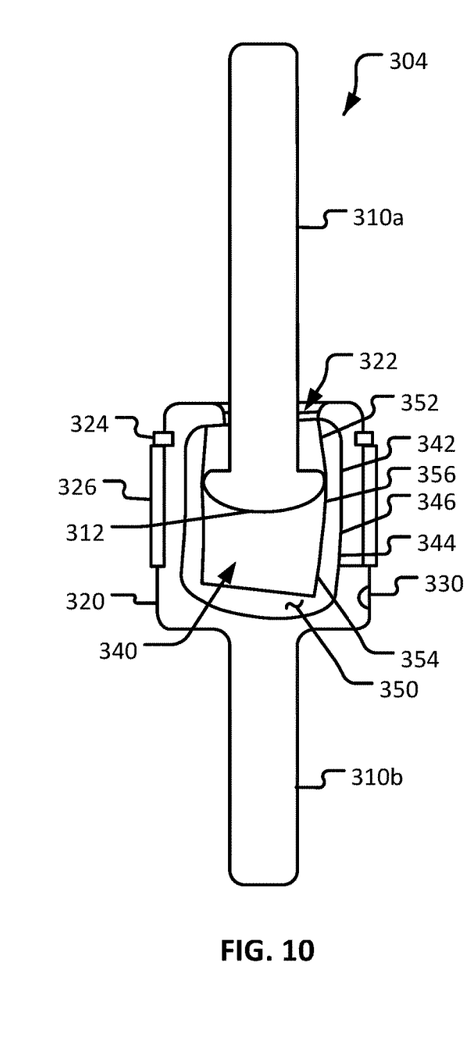
FIG. 10 is a longitudinal cross-sectional view of a second embodiment of the artificial facet joint device of FIG. 6.
Figure 11:
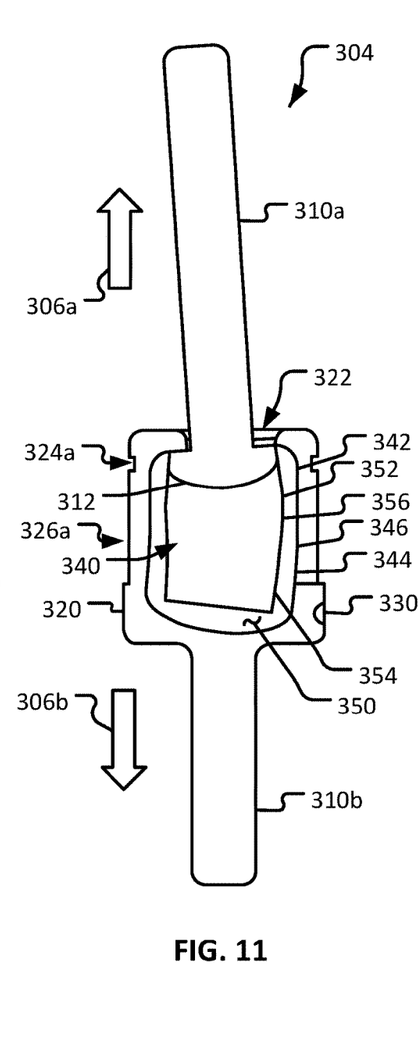
FIG. 11 is a longitudinal cross-sectional view of the artificial facet joint device of FIG. 10, in flexion.
Figure 12:
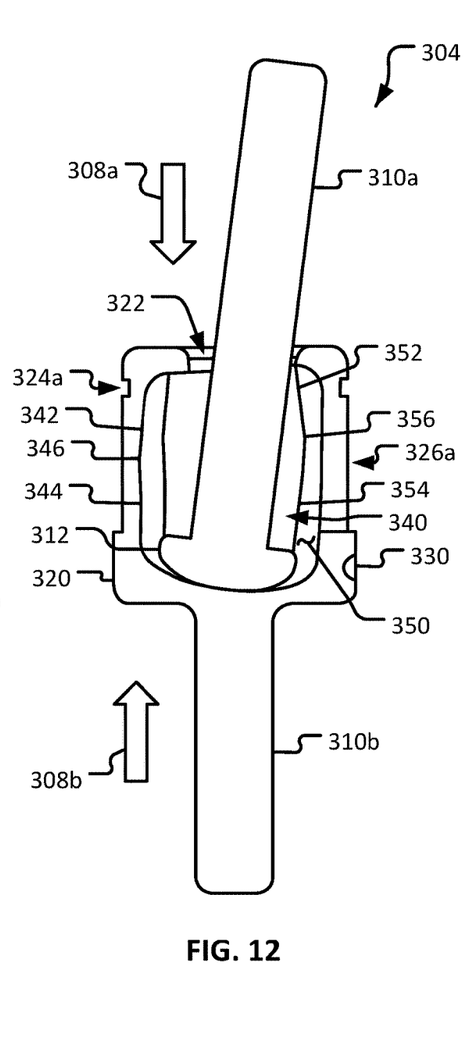
FIG. 12 is a longitudinal cross-sectional view of the artificial facet joint device of FIG. 10, in extension.

Referring to FIGS. 10-12, a facet joint replacement device 304 is an example of the types of facet joint replacement devices that can be used with artificial FJR system 100. Facet joint replacement device 304 can function as a piston/cylinder mechanism and can be substantially similar to facet joint replacement device 300. FIGS. 10-12 show a second embodiment of cross section A-A of FIG. 6.

First rod 310a can include a head 312. In some cases, head 312 can be located on a distal portion of first rod 310a. In some cases, head 312 can be rounded. In some cases, head 312 can be mushroom shaped. In some cases, head 312 can be rounded on a distal portion and flat on a proximal portion. In some cases, head 312 can extend perpendicular to the first rod 310a.

Housing 320 can be an elongate member that defines an internal space 340. End portion of rod 310a can be movably disposed within the internal space 340 of housing 320. In some cases, facet joint replacement device 304 can be installed such that the rod 310a and internal space 340 are in a neutral position with one another (i.e., no forces acting between the internal space 340 or the rod 310a). In some cases, head 312 can be movably disposed within the internal space 340 of housing 320.

Housing 320 can have various cross-sectional shapes. In some cases, the cross-sectional shape of the internal space 340 defined by housing 320 is circular, ovular, elliptical, polygonal, and the like. The cross-sectional shape of the internal space 340 can be selected to allow for a certain amount of free play between rod 310a and an internal wall of housing 320. In some cases, housing 320 can be designed to have some degree of compliance such that housing 320 can bend or flex while in use. In some cases, housing 320 can be designed to be rigid such that housing 320 substantially does not bend or flex while in use.

In some cases, internal space 340 can be defined by two or more distinct portions. In some cases, the interior of housing 320 can have an upper portion 342 and a lower portion 344, separated by a bend 346. In some cases, upper portion 342 and lower portion 344 can have a diameter that decreases as portions 342 and 344 extend away from bend 346. In some cases, the diameters of upper portion 342 and lower portion 344 can change uniformly. In some cases, the diameters of upper portion 342 and lower portion 344 can change uniquely for each of the upper portion 342 and lower portion 344. In some cases, bend 346 can be a single area where upper portion 342 and lower portion 344 meet. In some cases, bend 346 can be a separate portion with a uniform diameter along bend 346. In some cases, sections of upper portion 342 and/or lower portion 344 can have a consistent diameter before the diameter decreases. In some cases, bend 346 can be located at a point such that the movement of first rod 310a follows a natural trajectory of healthy facet movement. In some cases, bend 346 can have a diameter to allow for a certain amount of free play between rod 310a and an internal wall of housing 320. In some cases, the decrease in diameter of upper portion 342 and/or lower portion 344 can cause an increase of resistance as head 312 and/or first rod 310a moves further along upper portion 342 and/or lower portion 344.

In some cases, housing 320 can have an angled top and/or an angled bottom for the internal space 340 such that when head 312 abuts the top and/or bottom of the internal space 340, even contact is made between the head 312 of first rod 310a and housing 320. In some cases, when head 312 comes into contact with housing 320 during extension and flexion, head 312 can limit range of movement. In some cases, an internal diameter of housing 320 defining internal space 340 can follow an arc that replicates a natural trajectory of a healthy facet joint in extension and flexion.

In some cases, housing 320 can include an insert 350. In some cases, housing 320 can be configured to allow an insert 350 to be inserted and/or removed. In some cases, insert 350 can be interchangeable with another insert 350. In some cases, insert 350 can have an exterior diameter, or diameters, that align with the internal diameter of housing 320. In some cases, insert 350 can have a bottom and side. In some cases, insert 350 can define an opening that can align with opening 322. In some cases, the opening of insert 350 can be larger than the opening 322, such that the opening of insert 350 does not limit range of motion. In some cases, insert 350 can include a top that defines an opening, such that when head 312 moves upward (e.g., during flexion, as shown in FIG. 11), the head 312 abuts a portion of insert 350. In some cases, insert 350 defines an internal space. In some cases, head 312 can be sized to fit inside the internal space defined by the insert 350.

In some cases, the internal space defined by the insert 350 can be defined by two or more distinct portions. In some cases, the interior of insert 350 can have an upper portion 352 and a lower portion 354, separated by a bend 356. In some cases, upper portion 352 and lower portion 354 can have a diameter that decreases as portions 352 and 354 extend away from bend 356. In some cases, the diameters of upper portion 352 and lower portion 354 can change uniformly. In some cases, the diameters of upper portion 352 and lower portion 354 can change uniquely for each of the upper portion 352 and lower portion 354. In some cases, bend 356 can be a single area where upper portion 352 and lower portion 354 meet. In some cases, bend 356 can be a separate portion with a uniform diameter along bend 356. In some cases, sections of upper portion 352 and/or lower portion 354 can have a consistent diameter before the diameter decreases. In some cases, bend 356 can be located at a point such that the movement of first rod 310a follows a natural trajectory of healthy facet movement. In some cases, bend 356 can have a diameter to allow for a certain amount of free play between rod 310a and an internal wall of insert 350. In some cases, the decrease in diameter of upper portion 352 and/or lower portion 354 can cause an increase of resistance as head 312 and/or first rod 310a moves further along upper portion 352 and/or lower portion 354.

In some cases, insert 350 can have an angled internal bottom for the internal space such that when head 312 abuts the bottom of the internal space defined by the insert 350, even contact is made between the head 312 of first rod 310a and insert 350. In some cases, when head 312 comes into contact with insert 350 during extension and flexion, head 312 can limit range of movement. In some cases, an internal diameter of insert 350, defining the insert internal space, can follow an arc that replicates a natural trajectory of a healthy facet joint in extension and flexion.

In some cases, the insert 350 can be an elastic element. In some cases, the elastic element can be made of various materials and can be constructed in various manners. In some cases, the elastic element can be made of a mesh composite. In some embodiments, the elastic element can be an elastic polymeric element. In some cases, the elastic element can be made of a variety of different types of materials and combinations of materials. For example, elastic element can be made of polymeric materials such as, but not limited to, polyurethane, polyethylene, silicone, and other biocompatible elastomers. In some cases, the elastic element can be made of metallic materials such as, but not limited to, nitinol, stainless steel, titanium, titanium alloys, cobalt-chrome, and the like. In some cases, elastic element is solid, but in other cases, elastic element can be constructed for enhanced compliance and/or elasticity. For example, in some embodiments elastic elements, or portions thereof, can be molded, laser-cut, machined, braided, woven, etc. so that the compliance and/or elasticity of elastic element can be enhanced. In some cases, the insert 350 can provide a soft stop at a maximum range of motion in extension caused by forces 308a and/or 308b (as shown in FIG. 12) and/or flexion caused by forces 306a and/or 306b (as shown in FIG. 11). In some cases, insert 350 can include channels cut-out of the insert 350 to allow deformation and/or specific a specific amount of resistance.

Housing 320 can include a first portion 324a and second portion 326a. In some cases, first portion 324a and second portion 326a can be indents on an exterior of housing 320. In some cases, first portion 324a can aid in securing ring 324. In some cases, second portion 326a can aid in securing sleeve 326. In some cases, first portion 324a can have a depth greater than second portion 326a. In some cases, an exterior diameter of housing 320 can follow an arc that replicates a natural trajectory of a healthy facet joint in extension and flexion. In some cases, portions 324a and 326a can be two separate pieces of housing 320. In some cases, sleeve 326 and ring 324 can hold portions 324a and 326a of housing 320 together. In some cases, portions 324a and 326a can be used to allow housing 320 to receive head 312.

Figure 13:
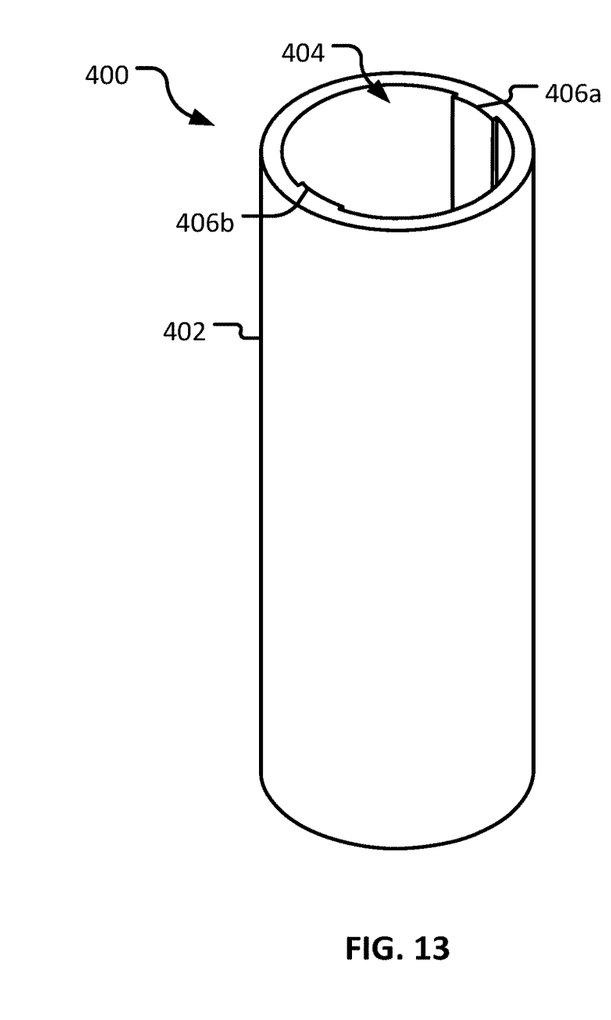
FIG. 13 is an isometric view of an example sleeve removal tool, in accordance with some embodiments provided herein.
Figure 14:
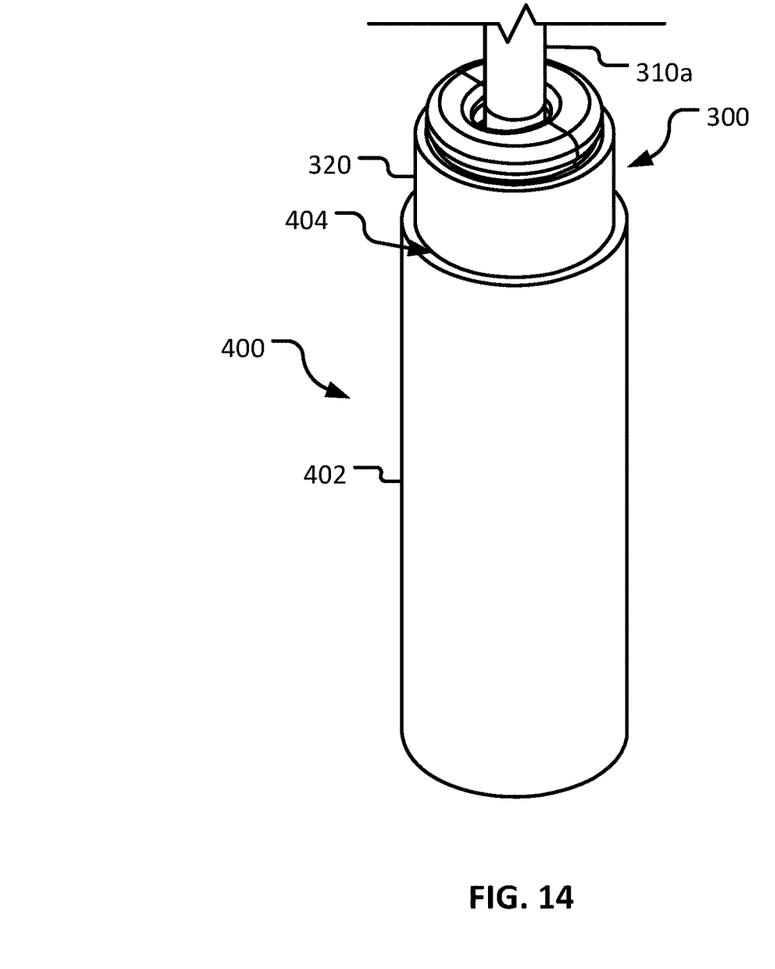
FIG. 14 is an isometric view of the sleeve removal tool of FIG. 13 being used with the artificial facet joint device of FIG. 6, in accordance with some embodiments provided herein.

Referring to FIGS. 13 and 14, a sleeve removal tool 400 can include housing 402. Housing 402 can define an internal chamber 404. In some cases, sleeve removal tool 400 can include one or more protrusions 406a and 406b.

In some cases, internal chamber 404 can extend through an entire length of housing 402. In some cases, internal chamber 404 can extend a portion of a length of housing 402. In some cases, internal chamber 404 can have a diameter that is substantially equal to or slightly larger than an outer diameter of sleeve 326, such that internal chamber 404 can receive facet joint replacement device 300.

In some cases, protrusions 406a and 406b can extend into internal chamber 404. In some cases, protrusions 406a and 406b can be sized and shaped such that recess 328 can receive one of protrusions 406a or 406b.

In some cases, sleeve removal tool 400 can be used to remove sleeve 326 from facet joint replacement device 300. For example, sleeve removal tool 400 can be pushed upward and protrusions 406a and 406b can be aligned with recess 328, such that a top of sleeve removal tool 400 abuts a bottom of sleeve 328. Sleeve removal tool 400 can then be pushed up, or tapped, to push sleeve 326 up housing 320, such that sleeve 326 can be removed.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A facet joint replacement device, comprising:
a housing defining a cylindrical outer profile, an elliptical opening, and an internal space, wherein the internal space has a diameter that is larger than the elliptical opening, and wherein the internal space defines a longitudinal axis that is arced and is for replicating a natural trajectory of a healthy facet joint in extension and flexion;
a first rod slidingly engaged with the opening, the first rod being linear and including an internal end portion slidably disposed within the internal space and an external end portion disposed outside of the internal space, the external end portion and the internal end portion each having circular cross-sections, the internal end portion comprising a head with a head diameter greater than a diameter of other portions of the first rod; and
a second rod integrally affixed to and extending directly from the housing opposite the opening such that the second rod is immovable relative to the housing,
wherein the diameter of the internal space decreases as the housing extends away from a horizontal axis of the housing, and wherein the head is sized such that resistance to movement between the head and the housing increases as the head moves along the decreasing diameter of the internal space.

2. The facet joint replacement device of claim 1, wherein the first rod and the second rod can be compressed toward each other such that a portion of the external end portion of the first rod enters the internal space.

3. The facet joint replacement device of claim 1, further comprising an elastic element disposed within the internal space, wherein the elastic element is disposed between the head and the opening.

4. The facet joint replacement device of claim 3, wherein the elastic element is coupled to the head.

5. A facet joint replacement device, comprising:
a housing defining a cylindrical outer profile, an elliptical first opening, and a first cylindrical internal space defining a first linear longitudinal axis, wherein the first internal space has a diameter that is larger than the elliptical first opening;
an insert defining a second opening and a second internal space, wherein the insert is configured to be disposed within the first cylindrical internal space, and wherein the second internal space defines a second longitudinal axis that is arced and is for replicating a natural trajectory of a healthy facet joint in extension and flexion;
a first rod slidingly engaged with the elliptical first opening, the first rod being linear and including an internal end portion slidably disposed within the second internal space and an external end portion disposed outside of the first internal space, the external end portion and the internal end portion each having circular cross-sections, the internal end portion comprising a head with a head diameter greater than a diameter of other portions of the first rod; and
a second rod integrally affixed to and extending directly from the housing opposite the first opening such that the second rod is immovable relative to the housing,
wherein an internal diameter of the insert decreases as the insert extends away from a horizontal axis of the insert, and wherein the head is sized such that resistance to movement between the head and the internal diameter of the insert increases as the head moves along the decreasing internal diameter of the insert.

6. The facet joint replacement device of claim 5, wherein the first rod and the second rod can be compressed toward each other such that a portion of the external end portion of the first rod enters the first internal space or the second internal space.

7. The facet joint replacement device of claim 5, wherein the insert is an elastic element.

* * * * *

UNITED STATES PATENT AND TRADEMARK OFFICE
CERTIFICATE OF CORRECTION

PATENT NO. : 11,737,793 B2
APPLICATION NO. : 16/757529
DATED : August 29, 2023
INVENTOR(S) : Mohamad Bydon et al.

Page 1 of 1

It is certified that error appears in the above-identified patent and that said Letters Patent is hereby corrected as shown below:

On the Title Page

Column 1 (item (22) PCT Filed), in Line 1, delete "Oct. 10," and insert -- Oct. 18, --.

Signed and Sealed this
Fifth Day of November, 2024

Katherine Kelly Vidal
*Director of the United States Patent and Trademark Office*